US012599555B2

(12) United States Patent
Cooper

(10) Patent No.: US 12,599,555 B2
(45) Date of Patent: Apr. 14, 2026

(54) FORMULATION

(71) Applicant: HEWLETT HEALTHCARE LIMITED, Leicestershire (GB)

(72) Inventor: Nigel Cooper, West Yorkshire (GB)

(73) Assignee: HEWLETT HEALTHCARE LIMITED, Leicestershire (GB)

( * ) Notice: Subject to any disclaimer, the term of this patent is extended or adjusted under 35 U.S.C. 154(b) by 978 days.

(21) Appl. No.: 17/763,249

(22) PCT Filed: Sep. 25, 2020

(86) PCT No.: PCT/GB2020/052333
§ 371 (c)(1),
(2) Date: Mar. 24, 2022

(87) PCT Pub. No.: WO2021/058977
PCT Pub. Date: Apr. 1, 2021

(65) Prior Publication Data
US 2022/0387315 A1       Dec. 8, 2022

(30) Foreign Application Priority Data
Sep. 27, 2019    (GB) ..................................... 1913952

(51) Int. Cl.
| | |
|---|---|
| A61K 9/06 | (2006.01) |
| A61K 31/352 | (2006.01) |
| A61K 31/465 | (2006.01) |
| A61K 31/4741 | (2006.01) |
| A61K 31/573 | (2006.01) |
| A61K 45/06 | (2006.01) |
| A61K 47/10 | (2017.01) |
| A61K 47/12 | (2006.01) |

(52) U.S. Cl.
CPC .............. *A61K 9/06* (2013.01); *A61K 31/352* (2013.01); *A61K 31/465* (2013.01); *A61K 31/4741* (2013.01); *A61K 31/573* (2013.01); *A61K 45/06* (2013.01); *A61K 47/10* (2013.01); *A61K 47/12* (2013.01)

(58) Field of Classification Search
CPC ....................................................... A61K 9/06
See application file for complete search history.

(56) References Cited

U.S. PATENT DOCUMENTS

| | | | |
|---|---|---|---|
| 5,549,894 A | 8/1996 | Hunt | |
| 5,576,346 A | 11/1996 | Clemente et al. | |
| 7,109,246 B1 * | 9/2006 | Hawtin | .................... A61P 17/02 |
| | | | 514/715 |
| 2014/0073616 A1 | 3/2014 | Marder | |
| 2019/0240193 A1 | 8/2019 | Palacios Peláez et al. | |

FOREIGN PATENT DOCUMENTS

| | | |
|---|---|---|
| EP | 0304802 B1 | 3/1993 |
| EP | 1079804 B1 | 12/2008 |
| GB | 2202145 B | 1/1991 |
| GB | 2337461 B | 10/2003 |
| JP | S63230641 A | 9/1988 |
| JP | H0196134 A | 4/1989 |
| JP | 2002530271 A | 9/2002 |
| WO | 2014095625 A1 | 6/2014 |
| WO | 2017097819 A1 | 6/2017 |

OTHER PUBLICATIONS

Shaikh et. al. (Journal of Chromatographic Science, vol. 47, Feb. 2009). (Year: 2009).*
Altounyan, et al. "Treatment of asthma with disodium cromoglicate (FPL 670, "Intal")" Respiration, 1969, pp. 131-140, vol. 26.
Altounyan, R. E. C. "Review of clinical activity and mode of action of sodium cromoglycate." Clinical & Experimental Allergy, 1980, pp. 481-489, vol. 10.
Ariyanayagam, M, et al., Topical sodium cromoglicate in the management of atopic eczema—a controlled trial, British Journal of Dermatology, 1985, pp. 343-348, vol. 112.
Bodor, Nicholas, et al., "Improved delivery through biological membranes VII. Dermal delivery of cromoglycic acid (cromolyn) via its prodrugs." International Journal of Pharmaceutics, 1980, pp. 63-75, vol. 7.1.
De Groot, Anton, et al., "Contact allergy to cocamidopropyl betaine." Contact Dermatitis, 1995, pp. 419-422, vol. 33.6.
Edwards, Alan M., et al., "The effects of topical sodium cromoglicate on itch and flare in human skin induced by Intradermal histamine: a randomised double-blind vehicle controlled intra-subject design trial." BMC research Notes 4.1, 2011, p. 1-7.
Edwards, Alan Martin, et al., "Systemic absorption of sodium cromoglicate from a new cutaneous emulsion (Altoderm®) in children with atopic dermatitis." EJD. European Journal of Dermatology, 2010, pp. 864-865, vol. 20.6.
Edwards, Alan Martin, et al., "Oral and topical sodium cromoglicate in the treatment of diffuse cutaneous mastocytosis in an infant." Case Reports 2011, pp. 1-6.
Gardner'S Chemical Synonyms and Trade Names, Gower Technical Press Lts, Hants, Engliand, Ninth edition, 1987, p. 651.
Haider, S. A. "Treatment of atopic eczema in children: use of topical sodium cromoglycate." The Mast Cell-Its Role in Health and Disease (ed J Pepys and AM Edwards). Pub Pitman Medical, Turnbridge Wells, England, 1979, pp. 570-576.

(Continued)

Primary Examiner — John S Kenyon
Assistant Examiner — Rehana Ismail
(74) Attorney, Agent, or Firm — Barnes & Thornburg LLP

(57) ABSTRACT

A composition, for example an oil-in-water emulsion, comprising an amphoteric surfactant, alkoxylated cetyl alcohol, a polar dmg and a preservative, wherein the total amount of preservative present in the composition is about 0.2% w/w or less and is not benzyl alcohol and/or triclosan. The drug may be sodium cromoglicate and/or nedocromil sodium. The formulation may be useful in the treatment of skin diseases such as atopic dermatitis.

18 Claims, 4 Drawing Sheets

(56) References Cited

OTHER PUBLICATIONS

Ishikura, T., et al. "Enhanced percutaneous absorption of ionizable water-soluble drugs." Drug design and delivery, 1987, pp. 285-295, vol. 1.4.

Kimata H, et al., "Topical cromolyn (disodium cromoglicate) solution in the treatment of young children with atopic dermatitis", Clin Exp Allergy, 1990, pp. 281-283, vol. 20.

Kjellman, N-I M, et al. Topical sodium cromoglicate in atopic dermatitis, Allergy, 1986, pp. 423-428, vol. 44(6).

Martindale, The Extra Pharmacopoeia, 29th Edition 1989. The Royal Pharmaceutical Society of Great Britain. Corticosteroids, Skin Disorders, pp. 880-881.

Martindale, The Extra Pharmacopoeia, 29th Edition 1989. The Royal Pharmaceutical Society of Great Britain. Sodium Cromoglycate, p. 1419.

Meffert, Hans, et al., "Disodium cromoglycate inhibits allergic patch test reactions." Contact dermatitis, 1985, p. 18-20, vol. 12.1.

Neale, M. G., et al. "The pharmacokinetics of sodium cromoglycate in man after intravenous and inhalation administration." British journal of clinical pharmacology, 1986, pp. 373-382, vol. 22.4.

Pike, M. G., et al., "Failure of a new topical sodium cromoglycate formulation to improve atopic dermatitis." European journal of pediatrics, 1988, pp. 170-178, vol. 148.2.

Stainer, R., et al. "Efficacy and acceptability of a new topical skin lotion of sodium cromoglicate (Altoderm) in atopic dermatitis in children aged 2-12 years: a double-blind, randomized, placebo-controlled trial." British Journal of Dermatology, 2005, vol. 152.2, pp. 334-341.

Stalder, J., et al., "European Task Force on Atopic Dermatitis. Severity Scoring of Atopic Dermatitis. The SCORAD Index." Dermatology, 1993, vol. 186, pp. 23-31.

Stevens, Michael T., et al., . "The effect of 4% sodium cromoglicate cutaneous emulsion compared to vehicle in atopic dermatitis in children—a meta-analysis of total SCORAD scores." Journal of Dermatological Treatment, 2015, pp. 284-290, vol. 26.3.

Williams, H. C., et al. "Validation of the UK diagnostic criteria for atopic dermatitis in a population setting." British Journal of Dermatology, 1996, pp. 12-17, vol. 135.1.

Zur, Eyal. "Topical use of sodium cromoglicate (cromolyn sodium) to treat atopic dermatitis and other skin allergies." International Journal of Pharmaceutical Compounding, 2012, pp. 386-393, vol. 16.5.

Hiratsuka, Sachie, et al. "Enhancement of in vitro spontaneous IgE production by topical steroids in patients with atopic dermatitis." Journal of allergy and clinical immunology, 1996, pp. 107-113, vol. 98.1.

https://www.sigmaaldrich.com/catalog/product/aldrich/z269271?lang=en&region=GB Accessed via internet Nov. 8, 2022.

http://www.merckmillipore.com/GB/en/product/Durapore-Membrane-Filter-0.45m,MM_NF-HVLP02500 Accessed via Internet Nov. 8, 2022.

https://www.mattek.com/product-category/tissue-models/epiderm/ Accessed via internet Nov. 8, 2022.

American College of Allergy, Asthma, & Immunology. Skin Allergy. Jun. 2023. https://acaai.org/allergies/allergic-conditions/skin-allergy/.

Burgess, et al., "The Immune and Renerative Response to Burn Injury", Cells. Sep. 29, 2022;11(19):3073.

Macri, et al., "Urticaria Pigmentosa", book reference from the NIH—National Library of Medicine.

Zhou, Xu-Yue, Chen, Kun, and Zhang, Jia-An, "Mast cells as important regulators in the development of psoriasis" Front Immunol. Nov. 3, 2022; 13:1022986.

International search report and written opinion for PCT/GB2020/052333, dated Jan. 18, 2021.

English translation of an Office Action dated Aug. 21, 2024 and issued in connection with JP Application No. 2022-519151, 3 pages.

* cited by examiner

FORMULATION

FOREIGN CLAIM FOR PRIORITY UNDER 35 U.S.C. § 119

This application is a National Stage application of International Application No. PCT/GB2020/052333 filed Sep. 25, 2020. This application also claims priority under 35 U.S.C. § 119 to Great Britain Patent Application No. GB1913952.6, filed Sep. 27, 2019, the contents of which are hereby incorporated by reference.

FIELD OF THE INVENTION

The present invention concerns compositions, for example an oil-in-water emulsion, comprising an amphoteric surfactant, alkoxylated cetyl alcohol, a polar drug and a preservative, wherein the total amount of preservative present in the composition is about 0.2% w/w or less and is not benzyl alcohol and/or triclosan. The drug may be sodium cromoglicate and/or nedocromil sodium. The composition may be useful in the treatment of skin diseases such as atopic dermatitis

BACKGROUND

The listing or discussion of an apparently prior-published document in this specification should not necessarily be taken as an acknowledgement that the document is part of the state of the art or is common general knowledge.

Sodium cromoglicate (termed cromolyn sodium in the USA and variously also known as disodium cromoglicate or disodium 5,5'-[(2-hydroxytrimethylene)dioxy]bis-[4-oxo-4H-1-benzopyran-2-carboxylate]) is known to have beneficial effects in the treatment of atopic conditions, particularly asthma. Some positive results have been obtained in clinical trials addressing its efficacy with regard to atopic dermatitis (AD) (also known as eczema or atopic eczema) and associated skin disorders.

Atopic dermatitis is an inflammatory skin disorder, affecting up to 10% of the paediatric population. It is characterised by extreme itching, a chronic relapsing course and specific distribution around the body. There is usually a family history of allergy and the condition starts in early infancy.

Typical treatment regimes are to use simple emollients or topical corticosteroids. Long-term use of topical corticosteroids may have undesirable side effects, particularly in children.

Topical preparations containing sodium cromoglicate have been attempted (ointments, aqueous solutions and creams) but their clinical effect has been disappointing. This may be due to low bioavailability of sodium cromoglicate in the dermis, which may arise from poor penetration of the skin. Sodium cromoglicate is likely to have poor skin penetration properties arising from its extremely polar nature.

There have been a number of attempts to treat AD using various topical formulations of sodium cromoglicate (SCG). The results of the reported clinical trials are variable. Zur (2012) reviewed the literature and concluded that the majority of studies that showed efficacy of topical SCG in AD had used formulations in which SCG was completely dissolved in the aqueous phase (creams, emulsions, aqueous solutions) and concluded that the formulation had a critical influence and needed specific agents and methods to ensure sufficient penetration of the active ingredient into the skin. It was also noted that the penetration of the SCG into the skin would be affected by the severity of AD.

Haider (1979) published further results on children (aged 2 to 14 years) with chronic eczema, treated with topical SCG (7.5% or 10%) over a period of 5 years. The formulation used was prepared by mixing SCG with liquid paraffin, before mixing with white soft paraffin. Parents were advised to rub the preparation into their child's skin for at least 5 minutes twice daily. The majority showed some response to SCG, although in many cases 0.1%-0.2% hydrocortisone or 0.01%-0.02% betamethasone valerate was also needed for one to two weeks during acute exacerbations.

In the 1980's Fisons developed a 4% oil in water cream formulation which appeared to have better skin penetration in model experiments. This was used in a clinical trial programme of which 3 trials were published (Kjellman N-I M and Gustafsson I M. Topical sodium cromoglicate in atopic dermatitis, *Allergy* (1986) 44(6): 423-428; Pike M G and Atherton D J., Failure of a new topical sodium cromoglicate formulation to improve atopic dermatitis, *Eur J Ped* (1988) 148(2): 170; and Ariyanayagam M, Barlow T J G, Graham P, Hall-Smith S P, Harris J M. Topical sodium cromoglicate in the management of atopic eczema—a controlled trial. *Br J Dermatol* (1985) 112: 343-348). Only one of these trials by Arianayagam et al showed positive effects. In this study, a significant effect was seen on the total eczema score after 9 and 12 weeks of treatment. It was also shown that the greatest effect was seen in those subjects with a Total Serum IgE of <500 U/ml. However, the skin penetration of this formulation was relatively poor with the calculated bioavailability of the applied dose ranging from 0.01% to 2.75%. This compares to a bioavailability of 10-15% when the drug is administered by inhalation in the treatment of asthma (Neale M G, Brown K, Hodder R W, Auty R M. The pharmacokinetics of sodium cromoglicate in man after intravenous and inhalation administration. *Br J Clin Pharmac* (1986) 22: 373-382).

In 1990 Kimata and Igarishi (Kimata H, Igarashii M I E. Topical cromolyn (disodium cromoglicate) solution in the treatment of young children with atopic dermatitis. *Clin Exp Allergy* (1990) 20: 281-283) published a 4 week, placebo-controlled, double-blind trial of 1% aqueous solution of sodium cromoglicate. After application of the aqueous solution the skin was occluded with white soft paraffin. All patients had moderate to severe atopic dermatitis with Total Serum IgE levels ranging from 100 to 8600 U/ml. The sodium cromoglicate treated group exhibited significant benefits on the skin after one week's treatment and on the itch and sleep disturbance after two weeks.

The results of topical sodium cromoglicate in atopic dermatitis are extremely variable. This may be result of the different formulations, or concentrations used or the patient population selected or a combination of all three. The concentrations used have ranged from 1% to 10% and the formulations include aqueous solution, creams and ointments. The most positive results have been seen in relatively young children (Range 6 months to 7 years) who are strongly atopic (Serum IgE>2SD from normal).

It is also probable that adequate skin penetration of the drug is an essential pre-requisite of clinical efficacy in order for the drug to attach to the receptors responsible for the allergic inflammation and itch. Sodium cromoglicate is an extremely polar compound and may have poor penetration of skin and mucous membranes. Little is known about its absorption through the skin in patients apart from the formulation used by Ariyanayagam et al which gave relatively low levels of absorption. Hiratsuka et al were unable to detect any sodium cromoglicate in the blood using a radioimmunoassay after applying an aqueous solution of the drug but it would seem unlikely that the drug was not absorbed in view of the demonstrated effects on B cell activity and on cytokine release. Sodium cromoglicate is not metabolised and is rapidly removed from the blood and the levels may have been below the level of detection. Urinary levels over time are probably a better measure of bioavailability. Haider encouraged his patients to rub the ointment into the skin (personal communication) which may have increased the penetration.

At the publication of the first Japanese trial the journal carried an editorial (28) which stated "Given the frequent adverse effects of therapeutic alternatives, it certainly seems worth pursuing the potential benefits of topical cromolyn solution. . . . An effective, safe new drug to be used in the treatment of this troublesome disease would be very welcome."

There is therefore a long-felt interest in and need for the development of an acceptable vehicle that allows adequate skin penetration of sodium cromoglicate, for use in the treatment of atopic dermatitis. So far, a suitable vehicle has not been found, despite much interest in the area. Such a vehicle may be useful in a product that may fit as a maintenance treatment, particularly in children, between simple emollients and topical corticosteroids which at present are the mainstay treatment for this condition.

Ariyanayagam et al, for example, report that Bodor et al (1980; *Int J Pharmaceut* 7, 63) have produced a series of lipophilic pro-drugs in an attempt to improve the bioavailability of sodium cromoglicate.

GB 2 202 145, describes several topical formulations of nedocromil sodium (sodium 9-ethyl-6,9-dihydro-4,6-dioxo-10-propyl-4H-pyrano(3,2-g)quinoline-2,8-dicarboxylate), including an oil-in-water emulsion.

Ishikura et al (1987) *Drug Design & Delivery* 1, 285-295 describes the use of amphoteric surfactants in improving percutaneous uptake of diltiazem hydrochloride (used as an example of a cationic water-soluble drug) from water-soluble films. Whilst investigation of uptake of sodium cromoglicate (used as an example of an anionic water-soluble drug) was also reported in the paper, the effect of the amphoteric surfactants on sodium cromoglicate uptake was not suggested or tested.

EP1079804 describes a composition, for example an oil-in-water emulsion, comprising an amphoteric surfactant, alkoxylated cetyl alcohol and a polar drug. However, these compositions lack long term stability and comprise high levels of preservatives, such as benzyl alcohol and triclosan, that can cause irritation to the skin.

DISCLOSURE OF THE INVENTION

The present work surprisingly shows that a stable composition, for example an oil-in-water emulsion, comprising an amphoteric surfactant, alkoxylated cetyl alcohol, a polar drug, for example sodium cromoglicate, wherein the total amount of preservative present in the composition is about 0.2% w/w or less of the composition may be formed. The composition has been found to be highly stable, and an effective amount of the drug may penetrate the skin of a patient when the formulation is applied topically. The composition may be useful in the treatment of skin diseases such as atopic dermatitis (AD).

The composition of the present invention avoids the use of cationic substances and provides a stable formulation, for example a stable emulsion, comprising the polar substance sodium cromoglicate that allows for effective absorption of SCG into the skin. Typically, the polarity of sodium cromoglicate limits the stability of known emulsions. The use of an amphoteric surfactant in combination with an alkoxylated cetyl alcohol may assist in overcoming this problem and may also assist the skin penetration of the sodium cromoglicate. Additionally, the composition of the invention provides a single formation that when applied to the skin delivers an aqueous solution of cromoglicate to the skin that is covered by a pleasant-to-use, non-sticky occlusive layer, in just one application.

The composition of the present invention also avoids the use of high levels (for example, greater than 0.2 w/w of the composition) of preservatives, but still eliminates or reduces the number and type of microorganisms in the composition to a level that is acceptable and/or meets regulatory approval and/or means that the composition does not degrade over time (i.e. eliminates or reduces the microbial load of the composition). In particular, the composition avoids the use of preservatives such as benzyl alcohol and/or triclosan, the use of which should be avoided or reduced to a minimum due to the potential to cause irritation, sensitivity or allergic reaction when applied to the skin.

Thus, the present invention provides a composition comprising an amphoteric surfactant, an alkoxylated cetyl alcohol and a polar drug, wherein the total amount of preservative present in the composition is about 0.2% w/w or less.

The composition is hereinafter referred to as the composition of the invention.

As used herein, the term "preservative" is intended to encompass chemical compounds that are present in the composition to prevent spoilage of the composition and not to treat diseases or conditions caused by microbes or bacteria. Examples of such preservatives include, but are not limited to, sorbic acid, sodium sorbate and sorbates, benzoic acid and benzoates, parabens, sulfur dioxide and sulfites, nitrites, nitrates, lactic acid, propionic acid and propionates, isothiazolinones, benzyl alcohol, triclosan and/or formaldehyde releasers.

For the avoidance of doubt, preferences, options, particular features and the like indicated for a given aspect, feature or parameter of the invention should, unless the context indicates otherwise, be regarded as having been disclosed in combination with any and all other preferences, options particular features and the like as indicated for the same or other aspects, features and parameters of the invention.

The term "about" as used herein, e.g. when referring to a measurable value (such as an amount or weight of a particular component in the reaction mixture), refers to variations of ±20%, ±10%, ±5%, ±1%, ±0.5%, or, particularly, ±0.1% relative to the specified amount. For example, a variation of ±0.5% with regards to the percentage of a component in the composition of the invention, means a variation of 0.5% relative to the percentage given, i.e. ±0.5% of 10% would mean a variation from 9.5% to 10.5%.

The composition may comprise an aqueous phase and an oil phase. It may be an emulsion or may be used in the manufacture of an emulsion. It may, for example, form or be comprised in the aqueous phase of an emulsion. It is preferred that the emulsion is an oil-in-water emulsion, but it will be appreciated that the emulsion may alternatively be a water-in-oil emulsion.

A "polar drug" is a compound which may be used as an active ingredient in a medicament that is water-soluble and ionises on solution in distilled water at 25° C. A "water-soluble" compound may be dissolved in distilled water at 25° C. at a ratio of compound to water (weight to volume, or volume to volume if the compound is a liquid) of at least 1 to 10000, 1 to 1000, 1 to 100, 1 to 30, 1 to 10, 1 to 1 or 1 to less than 1. It is preferred that the polar drug comprises an anionic polar drug, for example a chromone, such as nedocromil sodium and/or sodium cromoglicate. Most preferably, the drug comprises sodium cromoglicate.

Other examples of polar drugs that may be suitable include polar anti-inflammatory or antirheumatic agents, for example ibuprofen, antibacterial agents, for example agents that may be useful in the treatment of acne (for example clindamycin sodium phosphate or tetracycline); a hormone, for example an oestrogen; a polar analgesic, for example fentanyl; a polar motion-sickness treatment molecule, for example scopolamine or hyoscine; an antihypertensive, for example clonidine; a vasodilator or coronary vasodilator, for example nitroglycerine; or nicotine.

Further preferred examples of suitable polar drugs include a polar corticosteroid formulation, for example a salt of an esterified corticosteroid, for example a salt of a phosphate or succinate ester. Such polar formulations may be soluble in water and are the form commonly used for injections or solutions. Suitable salts of esters of corticosteroids include betamethasone sodium phosphate, dexamethasone sodium phosphate, hydrocortisone sodium phosphate, hydrocortisone sodium succinate, methylprednisolone sodium succinate and prednisolone sodium succinate.

The drug may be useful topically in treating skin disease or may be a drug that is useful when administered transdermally.

The drug, for example sodium cromoglicate, may constitute from about 0.01 to about 20% w/w, preferably from about 0.1 to about 20% w/w, still more preferably from about 1 to 10% w/w, yet more preferably about 7.5% w/w, most preferably about 4% w/w of the composition, for example the emulsion.

When the polar drug comprises a corticosteroid, the corticosteroid may preferably constitute 0.01 to 10% w/w, preferably from 0.1 to 10% w/w, most preferably about 0.25 or 0.5% w/w of the composition, for example the emulsion.

It will be appreciated that it is preferred that the above proportions are present in a composition of the invention that is a formulation, for example an emulsion, as may be administered to a patient, for example applied to the skin of the patient. It will further be appreciated that a composition of the invention may be useful in preparing a formulation, for example an emulsion, suitable for administration to a patient, for example application to the skin of a patient; for example, the composition may form the aqueous phase of the emulsion, or it may be a concentrate used in the preparation of the aqueous phase of the emulsion, as known to those skilled in the art. Thus, it will be appreciated that in these examples of compositions of the invention, it may be preferred that the proportion of the composition that is the polar drug may be from about 1.5 to about 10 times greater than that given above.

It will be appreciated that the composition, for example emulsion, may comprise more than one polar drug. Thus, for example, a preferred composition, for example emulsion, of the invention may comprise a chromone, such as nedocromil sodium and/or sodium cromoglicate, and a corticosteroid. The corticosteroid may constitute 0.01 to 10% w/w, preferably from 0.1 to 10% w/w, most preferably about 0.25 or 0.5% w/w of the emulsion or other formulation as administered to a patient, as above. Preferences for the corticosteroid are as given above; most preferably it is betamethasone sodium phosphate.

It is preferred that when the composition is in the form of an emulsion, the emulsion is stable. By this is meant that separation of the oil and water phases is not detectable by visual inspection after a period of at least six months, preferably at least one year, yet more preferably at least two or three years after manufacture when stored at 15° C. to 30° C. Storage may be at, for example, 22° C. For example, the composition of the invention in the form of an emulsion should have no significant change to its specification after storage at 25° C.±2° C./60% Relative Humidity±5% RH for at least six months, preferably at least one year, yet more preferably at least two or three years as defined in the International Council for Harmonisation of Technical Requirements for Pharmaceuticals for Human Use (ICH) guidelines.

It will be appreciated that the composition, for example emulsion, may be presented as a lotion or as a foam, as known to those skilled in the art.

The term "amphoteric surfactant" is well known to those skilled in the art. Such surfactants (which may also be known as ampholytic surfactants) possess at least one anionic group and at least one cationic group, and can therefore have anionic, non-ionic or cationic properties depending on the pH. If the isoelectric point of the molecule occurs at pH7, the molecule is said to be balanced. Amphoteric surfactants may have detergent and disinfectant properties. Balanced amphoteric surfactants may be particularly non-irritant to the eyes and skin.

Amphoteric surfactants are characterised by their ability to move between having a cationic or anionic charge dependent upon pH. In the presence of highly polar molecules such as sodium cromoglicate in a weak acid solution (for example, pH6), these surfactants may be compatible with the changes to charges around the molecule as it disassociates or associates (in the case of sodium cromoglicate, between the positive sodium and negative cromoglicate elements), providing a consistent medium for surface wetting and skin penetration.

It will be appreciated that the composition, for example emulsion, should not contain ingredients that may cause irritation to the skin, even on prolonged use. Compounds to which sensitisation may occur should be avoided. Thus, balanced amphoteric surfactants may be preferred.

The pH of skin is about 4.5. In order to avoid irritation to the skin, a pH that is slightly acidic, i.e. to the acid side of neutral, is preferred, for example a pH between about 4.5 and about 7.0. For example, the emulsion may be manufactured to a pH of 6.0, for example using sodium dihydrogen orthophosphate or citric acid as the buffer agent.

Examples of amphoteric surfactants include aminocarboxylic acids, aminopropionic acid derivatives, imidazoline derivatives (such as disodium cocoamphodiacetate), dodicin, pendecamaine or long-chain betaines, 2-alkyl-N-carboxymethyl-N-hydroxyethyl imidazolinium betaine, lauryldimethylaminoacetic acid betaine, 12 w/v % alkyldiaminoethylglycine hydrochloride, 3 w/v % alkyldiethylene-triaminoglycole hydrochloride, a mixture of alkyl betaines and alkyl amine oxides, N-tetradecyl-N,N-dimethyl-3-ammonio-1-propanesulfonate) or cocamidopropyl betaine. Any of these may be used, but cocamidopropyl betaine may not be preferred as instances of allergy to this compound, when used in shampoo, have been reported (De Groot et al (1995) *Contact Dermatitis* 33(6), 419-422).

It will be appreciated that an amphoteric surfactant may be supplied (as an "amphoteric surfactant" or amphoteric surfactant preparation) packaged or compounded with other substances by the manufacturer, and that references to an amphoteric surfactant encompass an amphoteric surfactant alone and a preparation supplied as an amphoteric surfactant by the manufacturer. It is preferred that the amphoteric surfactant is a carboxylated imidazoline derivative. It is particularly preferred that the amphoteric surfactant comprises disodium cocoamphodiacetate. It is still more preferred that the disodium cocoamphodiacetate is packaged or compounded with lauryl sulphate and hexylene glycol, as is known to those skilled in the art.

The amphoteric surfactant may constitute from about 0.1 to about 2% w/w by weight of the composition (such as the emulsion), for example from about 0.5 to about 1% w/w, such as about 0.9% w/w or about 0.92% w/w.

It is particularly preferred that the amphoteric surfactant is present in the composition in combination with sodium lauryl sulphate, hexylene glycol and sodium chloride.

In some compositions of the invention, the amphoteric surfactant may be present in the composition in combination with sodium lauryl sulphate, hexylene glycol and sodium chloride in the following amounts:

disodium cocoamphodiacetate from about 0.1 to about 2% w/w by weight of the composition (such as the emulsion), for example from about 0.5 to about 1% w/w, such as about 0.9% w/w or about 0.92% w/w;

sodium lauryl sulphate from about 0.05 to about 1% w/w or from about 0.1 to about 0.3% w/w, for example about 0.2% w/w or about 0.26% w/w;

hexylene glycol from about 0.01 to about 0.1% w/w or from about 0.05 to about 0.2% w/w, for example about 0.1% w/w or about 0.14% w/w; sodium chloride from about 0.01 to about 0.1% w/w, for example about 0.06% w/w.

For example, the composition of the invention may comprise an amphoteric surfactant, an alkoxylated cetyl alcohol and a polar drug, wherein the total amount of preservative (for example, chlorocresol) present in the composition is about 0.2% w/w or less and the composition further comprises disodium cocoamphodiacetate from about 0.1 to about 2% w/w by weight of the composition (such as the emulsion), for example from about 0.5 to about 1% w/w, such as about 0.9% w/w or about 0.92% w/w; sodium lauryl sulphate from about 0.05 to about 1% w/w or from about 0.1 to about 0.3% w/w, for example about 0.2% w/w or about 0.26% w/w; hexylene glycol from about 0.01 to about 0.1% w/w or from about 0.05 to about 0.2% w/w, for example about 0.1% w/w or about 0.14% w/w; and sodium chloride from about 0.01 to about 0.1% w/w, for example about 0.06% w/w.

The amphoteric surfactant may be incorporated in the water phase of an oil-in-water emulsion that is a preferred embodiment of the invention. This may assist skin penetration by the polar drug, for example sodium cromoglicate, and may hold the emulsion stable. In the absence of an amphoteric surfactant, the emulsion may break down over a period of 24 hours into two phases, i.e. the oils will separate and float to the surface.

It will be appreciated that when determining the percentage weight to weight of an ingredient of the composition, for example emulsion, or a solute to solvent, the weight in milligrams (mg) of the ingredient is compared with the weight in milligrams (mg) of the prepared composition, for example emulsion.

The term alkoxylated cetyl alcohol encompasses polypropoxylated cetyl alcohol, the chemical description given for Procetyl AWS in *Gardner's Chemical Synonyms and Trade Names*, ninth edition and PPG-5-Ceteth-20. Alkoxylated cetyl alcohol may be obtained from Croda Chemicals Ltd, Cowick Hall, Snaith, Goole, North Humberside, DN14 9AA. It is marketed as "Procetyl AWS". The alkoxylated cetyl alcohol may be useful for its water-soluble surface-active emollient properties. It may also act as an emulsifying and solubilising agent and imparts a silky feel to the skin.

The alkoxylated cetyl alcohol may constitute from about 0.1 to about 20% w/w, preferably from about 0.1 to about 10% w/w, still more preferably from about 0.5 to about 4% w/w of the emulsion and most preferably about 1% w/w of the composition (for example, the composition in the form of an emulsion).

It will be appreciated that it is preferred that the above proportions may be present in a composition of the invention that is a formulation (that is not necessarily an emulsion) that may be administered to a patient, for example applied to the skin of the patient. It will further be appreciated that a composition of the invention may be useful in preparing a formulation, for example an emulsion, suitable for administration to a patient, for example application to the skin of a patient; for example, the composition may form the aqueous phase of the emulsion, or it may be a concentrate used in the preparation of the aqueous phase of the emulsion, as known to those skilled in the art. Thus, it will be appreciated that in these examples of compositions of the invention, it may be preferred that the proportion of the composition that is the alkoxylated cetyl alcohol or amphoteric surfactant may be from about 1.5 to about 10 times greater than those given above.

It will be appreciated that the critical ingredients of the formulation, for example the emulsion, are the amphoteric surfactant, alkoxylated cetyl alcohol and the drug component (for example, sodium cromoglicate). Further ingredients may include water and an oil phase. Suitable components of the oil phase will be known to those skilled in the art, and the following description is not limiting.

It is preferred that the components of the composition, for example the composition in the form of an emulsion, are chosen such that the emulsion is acceptable to a patient using it. For example, it should not be too greasy. It is preferred that the emulsion has an appropriate viscosity for spreading smoothly over the skin with low friction over areas of broken or sensitive skin. Thus, the composition, for example the composition in the form of an emulsion may not have the appearance of a solid at 22° C. or at 37° C. It is preferred that the composition, for example the composition in the form of an emulsion may have a viscosity of from about 10, 20, 100, 200 or preferably 400 to about 20,000 centipoise or mPas at 22° C. or 37° C. It is further preferred that the composition, for example the composition in the form of an emulsion has a viscosity from about 1400 to about 2600 centipoise, preferably from about 2000 to about 2600 centipoise, when measured at a maximum shear rate of 210 $sec^{-1}$ and from about 2300 to about 3800 centipoise, preferably from about 3000 to about 3800 centipoise, when measured at maximum shear rate of 125 $sec^{-1}$.

Methods of measuring viscosity are well known to those skilled in the art and are described, for example, in Chapter 22 of *Remington's Pharmaceutical Sciences* 15th Ed, Mac Publishing. For comparison, the viscosity of olive oil is about 138 mPas at 10° C. and about 36 mPas at 40° C. The composition, for example the composition in the form of an emulsion, may be provided as a watery lotion, which may be applied via a bottle dispenser. More preferably, the composition, for example the composition in the form of an emulsion, may be provided as a cream which at 20° C. remains in an open container when the container is inverted, and may be dispensed using a hand pump attached to a bottle, such as may be used for dispensing liquid hand soap. Kjellman N-I M and Gustafsson I M., Topical sodium cromoglicate in atopic dermatitis. *Allergy* (1986) 44(6): 423-428, sets out some desirable characteristics of preparations for treating atopic dermatitis.

The composition of the invention is designed to "split" when worked onto the skin. Splitting results in a phase change of the composition into two layers, with the aqueous layer containing the cromoglicate being released onto the skin and then being covered by an occlusive oil layer. This allows the aqueous phase to quickly sink into the stratum corneum, leaving the occlusive layer behind on the skin.

Without wishing to be bound by theory, it is hypothesised that rubbing causes the emulsion to split, resulting in the white soft paraffin component becoming visible on the surface of the skin. In due course skin temperature causes this to melt and "disappear". The separation and subsequent melting of the heavier paraffin is thought to provide occlusion of the applied cromoglicate.

However, this characteristic can make viscosity difficult to measure by conventional means. An alternative method of measuring the viscosity of the composition of the invention is by penetrometry.

Methods of measuring penetration are well known in the art.

The composition of the invention, for example the composition in the form of an emulsion, may have a penetration at 25° C. of from about 10 mm to about 30 mm, such as from about 14 mm to about 28 mm.

The composition, for example the composition in the form of an emulsion, may appear as a foam which may be applied via a pressurised dispenser. When presented as a foam, it may be desirable for the composition, for example the composition in the form of an emulsion to be more dilute with regard to excipients and the same or more concentrated with regard to the polar drug than the composition, for example the composition in the form of an emulsion presented as a lotion, as described above. This may reduce the viscosity of the composition, for example the composition in the form of an emulsion and aid the dispensing of the foam.

The oil phase may comprise liquid paraffins, white soft paraffin, glycerol monostearate, emulsifying wax (such as a non-ionic emulsifying wax) or a lipophilic non-ionic surfactant (for example sorbitan tristearate), and/or isopropyl myristate.

These terms are well known to those skilled in the art.

Isopropyl myristate is an example of an emollient. Glycerol monostearate is an example of an emulsifying agent and may also act as an emollient.

The emulsifying wax (such as a non-ionic emulsifying wax) may be emulsifying wax BP (sodium lauryl sulphate BP and cetostearyl alcohol BP). Emulsifying wax (such as a non-ionic emulsifying wax) may be useful in the preparation of emulsions comprising polar substances. A lipophilic non-ionic surfactant, for example sorbitan tristearate, may be used as an alternative to or in addition to the emulsifying wax. For example, sorbitan tristearate may be contained in some emulsifying waxes.

Liquid paraffins and isopropyl myristate may act as emollients and form an occlusive film on the skin as water dries away from the emulsion. This film may assist in keeping the skin hydrated from the water applied in the emulsion.

Liquid paraffins may provide from about 2% to about 10% w/w of the composition, preferably from about 3% to about 6% w/w, still more preferably from about 4% to about 5% w/w and most preferably about 4.5% w/w or about 4.8% w/w of the composition.

White soft paraffin may provide from about 5% to about 20% w/w of the composition, preferably from about 7% w/w to about 15% w/w, still more preferably from about 10% to about 13% w/w and most preferably about 12% w/w of the composition.

The emulsifying wax (such as a non-ionic emulsifying wax or emulsifying wax BP, or lipophilic non-ionic surfactant, for example sorbitan tristearate), may provide from about 1% to about 15% w/w of the composition, preferably from about 2% to 10% w/w, still more preferably from about 6% to about 8% w/w, such as about 7% or about 7.2% w/w of the composition.

Isopropyl myristate may provide from 0.1 to 10% w/w, preferably 0.5 to 5% w/w, still more preferably about 2% w/w of the emulsion.

Typically, the oil phase may comprise (or consist or consist essentially of) emulsifying wax, liquid paraffin and soft white paraffin. The emulsifying wax, liquid paraffin and soft white paraffin may typically comprise greater than about 20% w/w of the composition, for example greater than about 22% w/w of the composition. For example, the composition of the invention may comprise (or consist or consist essentially of) emulsifying wax, liquid paraffin and soft white paraffin in an amount of from about 22% to about 26% w/w of the composition, such as about 24% w/w of the composition.

The aqueous phase comprises water, polar drug and preservatives, wherein the total amount of preservative present in the composition is about 0.2% w/w or less.

Disodium edetate (EDTA) and chlorocresol are suitable compounds with preservative properties. The drug may be in solution in the aqueous phase. EDTA may also contribute to the stability of the formulation by forming complexes with any heavy metal ions. Chlorocresol may have a residual antibacterial effect on the skin and may assist with limiting any damage at an eczema site arising from bacterial colonisation. The anti-infective effect of the preservative, for example chlorocresol may also serve to prevent potential infection from the prolonged rubbing process involved during administration.

It is preferred that the composition of the invention comprises less than about 0.1% w/w of benzyl alcohol, triclosan or mixtures thereof. For example, it is preferred that the composition of the invention comprises less than about 0.01% w/w of benzyl alcohol, triclosan or mixtures thereof and it is particularly preferred that the composition does not comprise benzyl alcohol and/or triclosan. For example, the composition may comprise from about 0.0001% w/w to about 0.1% w/w of the composition of benzyl alcohol, triclosan or mixtures thereof, such as from about 0.001% w/w to about 0.01% w/w.

In the composition of the invention, the preservative present in the composition may be chlorocresol, Chlorocresol may provide from about 0.001% to about 0.2% w/w of the composition, preferably from about 0.01% to about 0.15% w/w, still more preferably about 0.1% (such as 0.11% w/w) of the composition.

The composition of the invention (for example, in the form of an emulsion) may comprise, consist of or consist essentially of the components listed below, preferably in substantially the quantities listed below. It is preferred that the drug is sodium cromoglicate and/or nedocromil sodium, most preferably sodium cromoglicate.

US 12,599,555 B2

11

| Constituent | Inclusion rate % w/w of the composition |
|---|---|
| Sodium cromoglicate | from about 0.1 to about 20% w/w, for example from about 1 to 10% w/w, preferably about 4% w/w; |
| Emulsifying wax | from about 1% to about 15% w/w, for example from about 2 to 10% w/w, such as about 7% or about 7.2% w/w; |
| Liquid paraffin | from about 2% to about 10% w/w, for example from about 3% to about 6% w/w, such as about 4.5% w/w or about 4.8% w/w; |
| White soft paraffin | from about 5% to about 20% w/w, for example from about 7% to about 15% w/w, such as about 12% w/w; |
| Chlorocresol | from about 0.001% to about 0.2% w/w, for example from about 0.01% to about 0.15% w/w, such as about 0.1% or about 0.11% w/w; |
| Disodium cocoamphodiacetate | from about 0.1 to about 2% w/w by weight of the composition, for example from about 0.8 to about 1% w/w, for example about 0.9% w/w or about 0.92% w/w; |
| Sodium laurilsulfate | from about 0.05 to about 1% w/w, for example, from about 0.1 to about 0.3% w/w, for example about 0.2% w/w or about 0.26% w/w; |
| Hexylene glycol | from about 0.01 to about 0.1% w/w, for example, from 0.05 to about 0.2% w/w, for example about 0.1% w/w or about 0.14% w/w; |
| Sodium chloride | from about 0.01 to about 0.1% w/w, for example about 0.06% w/w; |
| Polypropoxylated cetyl alcohol (Procetyl AWS#) | from about 0.1 to about 20% w/w, for example from about 0.1 to about 10% w/w, such as about 1% w/w; |
| Citric acid monohydrate | from about 0.05 to about 1% w/w, such as about 0.1% w/w; |
| Purified water | to 100% |

It is to be understood that components and values defined above for the composition of the invention apply when the composition is in the form of an emulsion, and when the composition or emulsion is provided as a foam, cream or lotion.

For the avoidance of doubt, in this specification when we use the term "comprising" or "comprises" we mean that the extract or composition being described must contain the listed ingredient(s) but may optionally contain additional ingredients. When we use the term "consisting essentially of" or "consists essentially of" we mean that the extract or composition being described must contain the listed ingredient(s) and may also contain small (for example up to 5% by weight, or up to 1% or 0.1% by weight) of other ingredients provided that any additional ingredients do not affect the essential properties of the extract or composition. When we use the term "consisting of" or "consists of" we mean that the extract or composition being described must contain the listed ingredient(s) only.

It is also intended that the terms "comprise" or "comprises" or "comprising" may be replaced with "consist" or "consisting" or "consisting essentially of" throughout the application as required.

The pH of the emulsion may be adjusted to 6.0 using sodium dihydrogen orthophosphate or citric acid.

The composition of the invention, for example the composition in the form of an emulsion, may appear as a cream or a watery lotion. The lotion may be rubbed into the affected skin for about 3 to 5 minutes. During this process, the lotion may first go white, then clear and then disappear into the skin, leaving a protective barrier that may help to stop the skin drying out.

The composition of the invention, for example the composition in the form of an emulsion, may be prepared by methods well known to those skilled in the art. For example, it may be prepared by heating the oils to about 70° C., then adding them steadily to the water phase (also at or about 70° C.) with good stirring, and then allowing the emulsion to cool.

An example of a specific method is described below:

Approximately 90% of the purified water was placed into a suitable vessel for heating. Sodium cromoglicate was added to the water and heated until dissolved. Chlorocresol was then added to the water and mixed until dissolved. The aqueous mixture was then placed into a bulk manufacturing vessel. In a separate vessel some of the remaining purified water was added to sodium chloride and mixed until the sodium chloride was dissolved. Sodium lauryl sulfate, hexylene glycol and disodium cocoamphodiacetate were added to the aqueous sodium chloride solution and mixed until dissolved (this mixture is now known as Altocrom surfactant blend). White soft paraffin, liquid paraffin, emulsifying wax. The Altocrom surfactant blend and Procetyl AWS were then mixed together and heated. Meanwhile, citric acid was dissolved in the remaining purified water. Both mixtures were then added to the bulk manufacturing vessel and homogenized. The resulting composition was then cooled.

Once the composition of the invention, for example the composition in the form of an emulsion, has been formed, further water may be added with stirring if desired, for example in preparing a formulation suitable for delivery as a foam. A suitable formulation for delivery as a foam may be prepared by diluting the composition of the invention, for example the composition in the form of an emulsion essentially as described above by the addition of one-part water to two parts composition (for example emulsion). It will be appreciated that if the composition of the invention, for example the composition in the form of an emulsion is to be diluted before application to the skin that it may be preferred that the concentration of the drug, for example sodium cromoglicate, in the composition of the invention, for example the composition in the form of an emulsion may be calculated such that the desired concentration, for example 4%, is achieved in the diluted formulation. It will be appreciated that it is preferred that the composition of the invention, for example the composition in the form of an emulsion is formed with the composition that it is intended to apply to the skin, for example with the additional water referred to above ab initio so that dilution is not necessary.

A further aspect of the invention is a stable oil-in-water emulsion comprising sodium cromoglicate, wherein when the emulsion is applied to skin an amount of sodium cromoglicate penetrates the skin that is sufficient to produce a demonstrable effect in the treatment of atopic dermatitis/eczema.

The amount of sodium cromoglicate that penetrates skin may be measured by techniques well known to those skilled in the art, some of which are mentioned above. Methods include in vitro measurements on skin biopsies (which may be human or animal, preferably rodent, still more preferably hairless rat skin) or in vivo measurements. For example, the presence of sodium cromoglicate in plasma or urine following topical application to a human or experimental animal (for example rat or rabbit) may be measured. Such measurements are described in Ishikura et al (1987) cited above, and Ariyanayagam et al. Sodium cromoglicate may be quantified by techniques of analytical chemistry, for example high performance liquid chromatography (HPLC).

Effectiveness of the emulsion may be measured in animal models of atopic dermatitis, or in clinical trials on humans. Preferably it is measured in humans.

Patients having atopic dermatitis may be diagnosed by criteria known to the skilled person. For example, patients may be diagnosed by a general medical practitioner recognising the effect of atopic eczema on the surface of the skin. Several sets of criteria for diagnosis have been proposed in order to assist in achieving consistency between studies of the condition ((29) and Williams et al (1996) *B J Dermatol* 135, 12-17). The criteria discussed in Williams et al include: a history of an itchy skin plus three or more of: (i) a history of rash in the skin creases (folds of elbows, behind the knees, fronts of ankles or around the neck); (ii) a personal history of asthma or hay fever; (iii) a history of generally dry skin in the last year; (iv) onset under the age of 2; and (v) visible flexural dermatitis as defined by a photographic protocol.

The criteria by which an effect on atopic dermatitis may be judged are set out in European Task Force on Atopic Dermatitis. Severity scoring of atopic dermatitis: The SCO-RAD index. *Dermatology* (1993) 186: 23-3 1.

It may be necessary to select patients on the basis of the level of circulating IgE. Suitable IgE tests include an in vitro total IgE test and an in vitro specific IgE test, for example the UniCAP Total (or Specific) IgE tests sold by Pharmacia & Upjohn, which use the Allergen ImmunoCAPs as the allergen reagent.

It may be desirable or necessary for patients to be screened according to their IgE levels before treatment with sodium cromoglicate is undertaken. More specifically, patients with total serum IgE levels below 150 IU/ml may be less likely to respond to the treatment. It is preferred that the patient is a child between the ages of 6 months and 10 years with atopic dermatitis.

The present invention also provides a composition of the invention as defined previously for use in the treatment of a skin disease or condition.

Also provided is a method of treating a skin disease or condition wherein a composition of the invention as defined herein is applied to the skin of an individual affected by the disease or condition, and the use of a composition of the invention as described previously in the manufacture of a medicament for the treatment of a skin disease or condition.

In the use or method an additional drug may be applied to skin before, after or at the same time as the composition of the invention, which may or may not comprise further amounts of the same or a different drug.

The additional drug may be a polar drug, as discussed above. The composition of the invention may aid penetration of the additional drug, particularly an additional polar drug, through the skin by altering the nature of the barrier presented by the skin, as described above.

It will however be appreciated that the additional drug may be a non-polar drug, for example a non-polar drug useful in the treatment of a skin disease or condition, for example a non-polar form of a corticosteroid, as found, for example, in creams prepared for topical application, for example in Betnovate™, Eumovate™ or Aureocort™ cream, as described further below. It is preferred that when the additional drug is a non-polar drug, for example a non-polar form of a corticosteroid, it is applied to the skin before, after, or at the same time as the said composition of the invention, preferably substantially immediately before or substantially immediately after the said composition, most preferably, before or immediately before the said composition. The composition may form a film over the surface of the skin which is beneficial, for example in retaining moisture.

It is preferred that the skin disease or condition is a disease of humans, but may also be one that affects other mammals, for example cats, dogs or horses. The disease or condition may be any in which skin mast cells and/or delayed (cellular) hypersensitivity reactions and/or inflammation is thought to be involved.

For example, the disease or condition may be selected from atopic dermatitis, eczema, contact sensitivity, psoriasis, drug sensitivity reactions, apthous ulcers, Behçet's syndrome, pemphigus, urticaria, urticaria pigmentosa, pyroderma gangrenosum, chronic skin ulcers, skin ulcers associated with Crohn's disease, burns, insect stings/bites, herpetic infections, systemic sclerosis (systemic scleroderma), morphoea (circumscribed or localised scleroderma) and dermal nodular fibrosis.

The skin disease or condition may be being, may have been or may be further treated by application of a corticosteroid. It may be beneficial to treat a patient, particularly a patient with atopic dermatitis or eczema, with a combination of a cromone and a corticosteroid. The therapeutic effects of a cromone such as sodium cromoglicate and corticosteroids may not be wholly interchangeable, as described in Altounyan & Howell (1969) "Treatment of asthma with disodium cromoglicate (FPL 670, "Intal")" Respiration 26(suppl), 131-140 and in Altounyan (1979) *Proceedings of Allergy* (Pitman Medical). A minimum dose of corticosteroids may be necessary below which sodium cromoglicate is without clinical effect. Further, corticosteroids alone, even in high dosage, may not achieve the same therapeutic response as a lower dose of corticosteroid together with sodium cromoglicate. Haider (5) suggests that sodium cromoglicate may exert a corticosteroid-sparing effect in atopic eczema or that there may be a synergism between the two.

The cromone and corticosteroid may be presented in the same formulation or in separate formulations. The cromone and corticosteroid may be presented as separate formulations for topical application. Either or both formulations (if appropriate) may be a composition, for example an emulsion, of the invention. For example, a formulation comprising a corticosteroid may be applied before or after (preferably before) a composition of the invention comprising a cromone, for example sodium cromoglicate.

The corticosteroid may be in a polar or a non-polar form; preferably it is in a non-polar form if it is not presented in a composition of the invention. Suitable formulations comprising a non-polar corticosteroid include the proprietary formulations Betnovate RD (betamethasone valerate, ready diluted), Aureocort (triamcinolone acetonide and chlortetracycline hydrochloride (an antibiotic)), and Eumovate (clobetasone butyrate). A 1% hydrocortisone preparation may also be used.

It will be appreciated that betamethasone valerate and triamcinolone acetonide may be considered to be potent corticosteroids, and clobetasone butyrate may be considered to be a moderately potent corticosteroid, as classified, for example, in Martindale, the Extra Pharmacopoeia, 31st Edition. Hydrocortisone may be considered to be a mild corticosteroid. It will be appreciated that the corticosteroid preparation used in combination with an emulsion of the invention comprising a cromone may be chosen depending upon the severity of the symptoms to be treated. A stronger (for example, moderately potent or potent) corticosteroid may be used at the start of combination therapy, which may be replaced by a weaker (for example a mild or moderately potent) corticosteroid as the symptoms are brought under control. Thus, if the symptoms are exacerbated, for example as the result of the patient contracting a cold, then a stronger corticosteroid may be used until the symptoms are diminished, whereupon a weaker corticosteroid may be used.

Symptoms that may be assessed include skin itching, sleep loss and skin condition, for example redness and the presence of sores or scabs.

The composition of the invention comprising sodium cromoglicate and/or nedocromil sodium, may also be useful in the treatment of sunburn or in sunscreen preparations. The composition may also be useful in cosmetic preparations, for example anti-ageing creams.

Also provided is a composition of the invention as herein defined for use in the treatment of a patient in need of a polar drug, for example by topical or transdermal administration.

Also provided is method of delivering a polar drug to a patient in need thereof which method comprises administering a composition of the invention as defined herein.

The present invention also provides a method of treatment of a patient in need of a polar drug comprising applying a composition of the invention as previously defined comprising the said polar drug to the skin of the said patient and the use of a composition of the invention in the manufacture of a medicament for treating a patient in need of a polar drug, for example by topical or transdermal administration.

The polar drug may be or may comprise, for example, a polar anti-inflammatory or antirheumatic agent, for example ibuprofen; an antibacterial agent, for example an agent that may be useful in the treatment of acne (for example clindomycin sodium phosphate or tetracycline); a hormone, for example an oestrogen; a polar analgesic, for example fentanyl; a polar motion-sickness treatment molecule, for example scopolamine or hyoscine; an antihypertensive, for example clonidine; a vasodilator or coronary vasodilator, for example nitroglycerine; or nicotine.

The patient in need of a polar drug may be, for example, a patient with arthritis that is in need of a polar anti-inflammatory or antirheumatic agent, for example ibuprofen. Alternatively, the patient in need of a polar drug may be a patient with acne that is in need of a polar antibacterial drug, for example clindamycin sodium phosphate or tetracycline. The patient in need of a polar drug may be a patient in need of nicotine, for example a patient who is attempting to give up cigarette smoking. Polar drugs that may be suitable for treating particular conditions when administered transdermally will be known to those skilled in the art.

The composition of the invention (for example where the composition is in the form of an emulsion) may be packaged or presented in any convenient way. For example, it may be packaged in a tube, tub, bottle or pressurised aerosol, using techniques well known to those skilled in the art and as set out in reference works such as *Remington's Pharmaceutical Sciences* 15th Ed, Mac Publishing. It is preferred that it is packaged in such a way as to minimise contact of the unused composition or emulsion with the environment, in order to minimise contamination of the composition or emulsion both before and after the container is opened. It is particularly preferred that the composition or emulsion is packaged in a pressurised aerosol container or in a plastic dispenser bottle. For example, an emulsion comprising sodium cromoglicate at either about 4% or about 8% w/w may be packaged in a plastic dispenser bottle, which may contain one month's supply (between about 150 and 300 ml).

It will be appreciated that the composition of the invention, for example the composition in the form of an emulsion may be provided as a cream or a lotion, or a foam.

The composition of the invention (for example the composition in the form of an emulsion) may be applied topically or transdermally to affected areas or prophylactically to unaffected areas. The composition of the invention, for example the composition in the form of an may be applied as directed by a physician. For example, the affected area may be rubbed, for example for at least about 5 minutes, to apply the composition of the invention, for example the composition in the form of an emulsion in order to encourage absorption of the drug. The composition of the invention, for example the composition in the form of an may be applied once or twice a day, or at greater or lesser intervals, depending upon the needs of the patient, as determined by the patient or a physician. As described above, a composition of the invention, for example the composition in the form of an emulsion, comprising a cromone may be applied before, after or at the same time as a formulation comprising a corticosteroid.

The invention will now be described by reference to the following, non-limiting, figures and examples.

EXAMPLE 1

Figure 1:
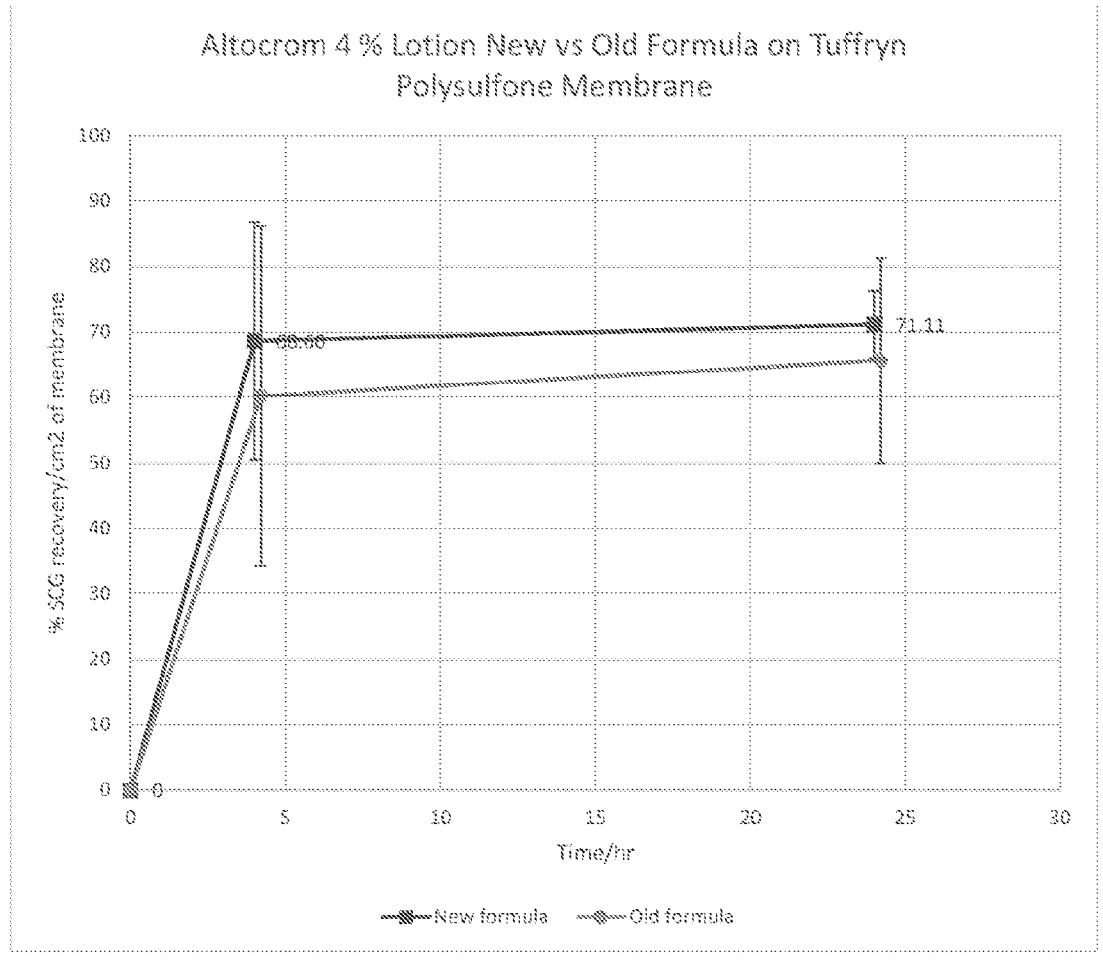
FIG. 1: Graph showing a comparison between a 4% sodium cromogycate composition of the invention and a reference composition using Tuffryn Polysulfone Membrane.

Preparation of a Composition of the Invention in the Form of an Oil-in-Water Emulsion Comprising Sodium Cromoglicate The following substances are combined to form an emulsion. The percentages refer to percentages w/w of the final emulsion.

Group A

| | |
|---|---|
| Emulsifying wax | 7.2% w/w |
| Liquid paraffin | 4.8% w/w |
| White soft paraffin | 12% w/w |

Group B

| | |
|---|---|
| Sodium cromoglicate | 4% w/w |
| Chlorocresol | 0.11% w/w |
| Disodium cocoamphodiacetate | 0.92% w/w |
| Sodium lauryl sulfate | 0.26% w/w |
| Hexylene glycol | 0.14% w/w |
| Sodium chloride | 0.06% w/w |
| Procetyl AWS# | 1% w/w |
| Citric acid monohydrate | 0.1% w/w |
| Purified water | 69.41% w/w |

The emulsion was generally prepared by heating the oils (for example, the compounds in group A) to about 70° C., then adding them steadily to the water phase (for example, the compounds in Group B; also at or about 70° C.) with good stirring, and then allowing the emulsion to cool.

Batches of about 10 litres to about 500 litres or more were prepared. The emulsion was prepared using a high shear homogeniser, as known to those skilled in the art. The mixture was stirred as the ingredients were mixed and stirring continued until the mixture cooled to room temperature.

An example of a specific method is as described below:

Approximately 90% of the purified water was placed into a suitable vessel for heating. Sodium cromoglicate was added to the water and heated until dissolved. Chlorocresol was then added to the water and mixed until dissolved. The aqueous mixture was then placed into a bulk manufacturing vessel. In a separate vessel some of the remaining purified water was added to sodium chloride and mixed until the sodium chloride was dissolved. Sodium lauryl sulfate, hexylene glycol and disodium cocoamphodiacetate were added to the aqueous sodium chloride solution and mixed until dissolved (this mixture is now known as Altocrom surfactant blend). White soft paraffin, liquid paraffin, emulsifying wax. The Altocrom surfactant blend and Procetyl AWS were then mixed together and heated. Meanwhile, citric acid was dissolved in the remaining purified water. Both mixtures were then added to the bulk manufacturing vessel and homogenized. The resulting composition was then cooled.

EXAMPLE 2

Preservative Optimisation

Nine compositions were prepared substantially as defined in Example 1, except for different preservatives and different amounts of preservatives were present in the compositions as shown in Table 1 below.

The microbiological stability was of each formulation was challenged using the method of the European Pharmacopoeia.

TABLE 1

Comparison of the microbiological stability of compositions using different preservatives and different preservative amounts.

| Sample | Amount and Type of Preservative % w/w | | | |
|---|---|---|---|---|
| Number | Triclosan | Benzyl Alcohol | Chlorocresol | Result |
| 1 | 0.2 | — | — | Fail |
| 2 | — | — | 0.1 | Pass |
| 3 | — | 0.2 | — | Fail |
| 4 | 0.2 | 0.2 | — | Fail |
| 5 | 0.2 | — | 0.1 | Pass |
| 6 | — | 0.2 | 0.1 | Pass |
| 7 | 0.2 | 0.2 | 0.2 | Pass |
| 8 | 0.18 | 0.18 | 0.09 | Pass |
| 9 | 0.2 | 0.2 | 0.1 | Pass |

The result show that it is possible to reduce the concentration of the preservative present in the composition to 0.1% w/w and eliminate the use of triclosan and benzyl alcohol from the composition, with compositions within the scope of the invention showing a microbiological pass using chlorocresol alone at 0.1% w/w.

This result is unexpected and advantageous as the use of benzyl alcohol and/or triclosan, have the potential to cause irritation, sensitivity or allergic reaction when applied to the skin. Therefore, their use should be avoided or reduced to a minimum.

EXAMPLE 3

Determination of the Lowest Effective Level of Preservative

Five Altocrom compositions were prepared as defined in Example 1, except that the amount of chlorocresol preservative in the composition was varied as shown in Table 2 below.

The microbiological stability was of each formulation was challenged using the method of the European Pharmacopoeia.

TABLE 2

Evaluation of lowest level of preservative.

| Amount of Preservative in Composition | Test Result |
|---|---|
| 0.11% | Pass |
| 0.08% | Pass |

EXAMPLE 4

Bioavailability of a Composition of the Invention as Prepared in Example 1

The bioavailability of the composition of the invention was first investigated using a vertical diffusion cell test system.

Details of Vertical Diffusion Cell Test System

The HDT 1000 Vertical Diffusion Cell Test System was used for the studies. This system accommodates 10 diffusion cells which are situated in a heated aluminium block with a magnetic stirrer positioned under each cell.

Cells

The cell is a Type "B" cell as described in Chapter <1724> of the current US Pharmacopeia USP24—NF19 and has an aperture of 1 cm$^2$ and a volume of ~7 ml without the presence of the magnetic stirrer bar. The cell is made of inert borosilicate glass and fitted with a side sampling arm.

The cells contents were continuously stirred during the operation by the magnetic stirrer bar to ensure homogenous distribution of temperature and adequate mixing of contents. An "open" cell top was used for the studies.

Vacuum Deaeration Apparatus for Receptor Medium Preparation

One of the main problems with Vertical Cell Diffusion Testing is the accumulation of air bubbles on the underside of the membrane, therefore the apparatus was degassed prior to use.

The receptor media was degassed by heating it to 45° C. under a vacuum of −90 kPa whilst stirring. This system produced media with oxygen levels below 4 ppm.

Altocrom 4% Lotion Samples

Materials

Altocrom 4% Lotion made using the method described in Example 1.

Membranes

The synthetic membranes used in this study were as follows:

HT Tuffryn Polysulfone Membranes

The Tuffryn Polysulfone membrane is a relatively inert hydrophilic polymeric membrane with a pore size of 0.45 μm. Manufactured by PALL.

https://www.sigmaaldrich.com/catalog/product/aldrich/z269271?lang=en®ion=GB

PVDF Membranes

PVDF Membrane Cat No HVLP02500 is a hydrophilic polymeric membrane with a pore size of 0.45 μm. Manufactured by Merck.

http://www.merckmillipore.com/GB/en/product/Duropore-Membrane-Filter-0.4m,Mm_NF-HVLP02500

PVDF Membrane Cat No. HVHP02500 is a hydrophobic membrane with a pore size of 0.45 μm.

http://www.merckmillipore.com/GB/en/product/Duropore-Membrane-Filter-0.45m,MM_NF-HVHP02500

EpiDerm

EpiDerm membranes are Reconstructed Human Epidermis (RHE). They are composed of normal, human-derived epidermal keratinocytes (NHEK) cultured on specially prepared tissue culture inserts.

EpiDerm has a human epidermal tissue structure and cellular morphology. It has a 3D structure consisting of organised and proliferative basal cells, spinous and granular layers and cornified epidermal layers.

EpiDerm Part Numer EPI-606 was used for this study and was supplied by MatTek Corporation. Supplier's storage and preparation instructions were followed to prepare the EpiDerm prior to the testing.

https://www.mattel.com/product-category/tissue-models/epiderm/

Receptor Medium

Phosphate buffered saline (PBS) solution containing streptomycin (0.1 mg/ml) and penicillin (100 units/ml) was used as the receptor fluid. This was prepared by adding five tablets of PBS with Penicillin-Streptomycin (10 ml) and making up to 1 l. This was degassed as described above.

Vertical Diffusion Cell Preparation

The Vertical Diffusion Cells were prepared by firstly adding a stirrer bar and then filling with degassed receptor medium (Phosphate Buffered Saline (PBS) Solution containing streptomycin (0.1 mg/ml) and penicillin (100 units/ml) as described above). The cell body was filled with the media to give a positive meniscus at the top of the cell to reduce any air being trapped under the membrane.

The assembled sample holder (open top) with the selected membrane was then placed on top of the cell body with the membrane contacting the receptor media.

The cell was checked for any air bubbles and then Parafilm wrapped around the joint between the cell top and body.

The prepared cell was placed in the heating block whilst the other cells were being prepared to maintain the required temperature of 32° C.

When all the cells had been filled with receptor media, the cell was removed with the holder and placed on a 4 dp balance. The Altocrom 4% Lotion was applied to the membrane with a 10 μl displacement micropipette and the exact mass recorded. The cream was then evenly distributed over the membrane with the end of a small glass rod. The time when the cream was applied was recorded as t=0. A layer of Parafilm was used to cover the open top of the cell.

For comparing the old and new formulation, 5 cells were dosed with the composition as prepared in Example 1 and 5 cells with a comparative composition.

Receptor Media Sampling

Sampling of the receptor media was carried out at the desired time points. Prior to sampling (approx. 10 min), the volume in the cell was checked against the calibration mark and refilled if required. Sampling was carried out using 100 μl displacement micropipette. 100 μl of the receptor fluid was placed in a glass HPLC vial with 300 μl insert. The receptor fluid was replaced immediately after sampling.

HPLC Analysis to Determine Sodium Cromoglicate (% w/w) in Receptor Medium

The following method describes the analysis to determine the sodium cromoglicate present in the receptor medium.

Mobile Phase: 77% Purified Water/23% Acetonitrile. Adjusted to pH 1.95-2.05 with Orthophosphoric Acid.

PBS Solution: 5 tablets of Phosphate Buffered Saline and 10.0 ml of Penicillin—Streptomycin made up to 1 l with purified water.

Standard Stock Solution: The Approved Reference Standard of Sodium Cromoglicate was accurately weighed to give 0.40 g±0.04 g ($W_1$). This was added to a 100 ml volumetric flask and dissolved in purified water and made up to volume.

Calibration Standard Solution: The appropriate concentration was selected for the analysis being carried out As an example, for a 400 ppm calibration standard solution, 10.0 ml of the standard stock solution was pipetted into a 100 ml volumetric flask and diluted to 100 ml with PBS solution. This was equivalent to 400 ppm.

This can be diluted further with PBS to obtain the appropriate concentration to calibrate at lower concentration levels.

Conditions

Column: 4 μm SYNERGI Polar-RP 25-mm×4.6 mm (or chemically or physically equivalent)

Flow rate (ml/min): 2.0

Detector Wavelength (nm): 325

Injection Volume (μl): 20

Oven Temperature: 30° C.

Approx. retention times (min): Sodium cromoglicate 3-5 min

Approx, Total Run Length: 15 min

Calculations for Chromeleon Software/Integrator

TABLE 3

| Peak Table | | | |
|---|---|---|---|
| Peak | Name | Amount | Response Factor |
| 1 | Sodium Cromoglicate | ($W_1$/0.4) × c | 1.0 |

TABLE 4

| Sequence (Sample List) | | | |
|---|---|---|---|
| Type | Weight | Dilution Factor | ISTD Amount |
| STD | 1.0 | 1.0 | 1.0 |
| SAMPLE | 1.0 | 0.7 | 1.0 |

Results

Tuffryn Polysulfone Membrane

The procedure described in the Vertical Diffusion Cell Preparation section detailed above was carried out using the Tuffryn Polysulfone membrane and pre-wetting the membrane was carried out.

Sampling was carried out at 4 and 24 hr and the results are shown in Table 5 and FIG. 1.

TABLE 5

| | % SCG recovery/cm$^2$ of membrane | |
| --- | --- | --- |
| Time/hr | Comparative composition | Composition of Example 1 |
| 0 | 0 | 0 |
| 4 | 60.20 ± 25.9 | 68.60 ± 18.21 |
| 24 | 65.60 ± 15.59 | 71.11 ± 5.20 |

Percentage of SCG recovery

The results showed that both compositions provided significant levels of time dependent penetration of cromoglicate from the compositions, with up to 65% achieved after 5 hours for the comparative composition and up to 71% achieved after 5 hours for the composition of Example 1.

PVDF (Hydrophilic) Membrane

The same method was carried out as described in the Vertical Diffusion Cell Preparation section detailed above. Pre-wetting the membrane was found to leave a varying amount of PBS solution on the surface of the membrane which caused the cream to be quickly diluted by an unknown quantity and added to experimental error. The membranes were therefore used without pre-wetting but were observed to hydrate very quickly with the PBS solution in the body of the Vertical Diffusion Cell.

Figure 2:
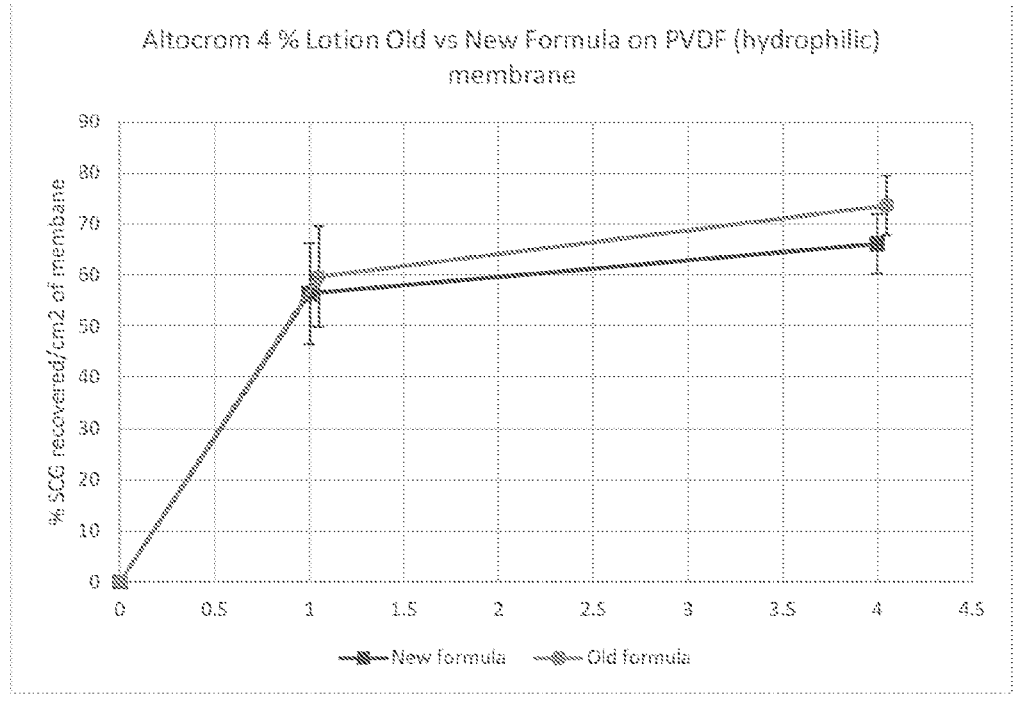
FIG. 2: Graph showing a comparison between a 4% sodium cromogycate composition of the invention and a reference composition using PVDF (hydrophilic) Membrane.

The SCG recovery is shown in Table 6 and FIG. 2.

TABLE 6

SCG recovery using PVDF membrane

| | % SCG recovery/cm$^2$ of membrane | |
| --- | --- | --- |
| Time/hr | Comparative composition | Composition of Example 1 |
| 0 | 0 | 0 |
| 1 | 59.68 ± 9.84 | 56.40 ± 4.44 |
| 4 | 73.64 ± 5.80 | 66.12 ± 8.07 |

The results showed that both compositions provided significant levels of time dependent penetration of the cromoglicate from the compositions, with up to about 60% achieved after 1 hour for both compositions.

PVDF (Hydrophobic) Membranes

The same method was carried out as described in the Vertical Diffusion Cell Preparation section detailed above. The hydrophobic nature of the membranes was found to make pre-wetting very difficult. Therefore the method was conducted without pre-wetting the membrane.

It was apparent that the percentage of the sodium cromoglicate recovered reached a maximum quickly so the samples were not continued for 24 hr.

Figure 3:
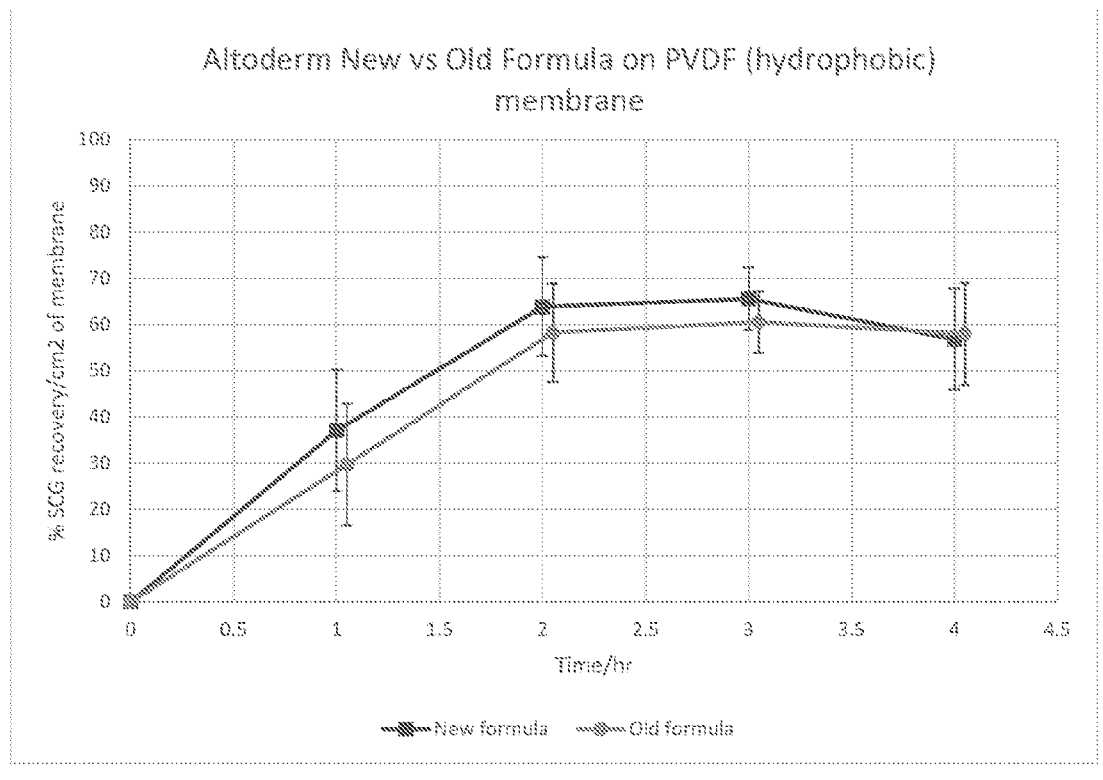
FIG. 3: Graph showing a comparison between a 4% sodium cromogycate composition of the invention and a reference composition using PVDF (hydrophobic) Membrane.

The results are shown in Table 7 and FIG. 3.

TABLE 7

SCG recovery using PVDF membrane

| | % SCG recovery/cm$^2$ of membrane | |
| --- | --- | --- |
| Time/hr | Comparative composition | Composition of Example 1 |
| 0 | 0 | 0 |
| 1 | 29.72 ± 13.11 | 37.05 ± 28.18 |
| 2 | 58.21 ± 10.67 | 63.87 ± 6.37 |
| 3 | 60.51 ± 6.72 | 65.51 ± 4.14 |
| 4 | 58.02 ± 11.02 | 56.80 ± 12.07 |

The results showed that both compositions provided significant levels of time dependent penetration of the cromoglicate from the compositions, with up to 60% achieved after 3 hours for the comparative composition and up to 65% achieved after 3 hours for the composition of Example 1.

EpiDerm

The membrane was stored and prepared as specified by the supplier instructions. Prior to use, the EpiDerm membranes were removed from the inserts they were supplied in using forceps and carefully transferred (with the supporting PTFE membrane underneath) and placed in pre-warmed assay medium at 37° C. The EpiDerm was incubated for 1 hr prior to use.

Figure 4:
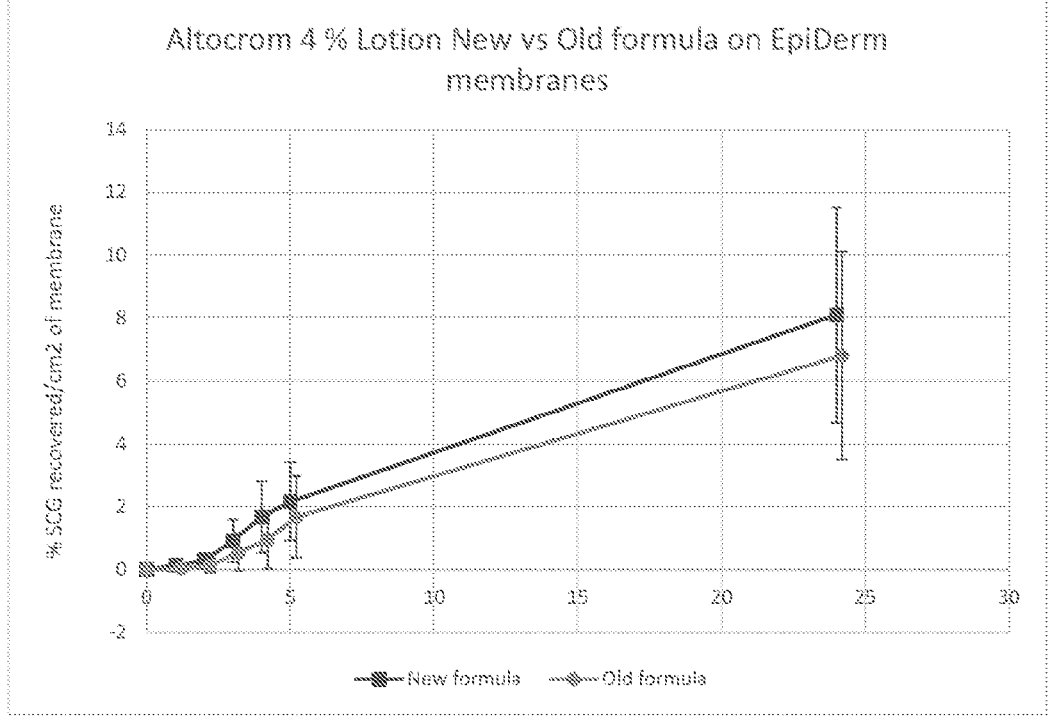
FIG. 4: Graph showing a comparison between a 4% sodium cromogycate composition of the invention and a reference composition using EpiDerm Membrane.

Sampling was carried out after 1, 2, 3, 4 and 24 hr and the results are shown in Table 8 and FIG. 4.

TABLE 8

SCG recovery using EpiDerm membrane

| | % SCG recovery/cm$^2$ of membrane | |
| --- | --- | --- |
| Time/hr | Comparative composition | Composition of Example 1 |
| 0 | 0 | 0 |
| 1 | 0.02 ± 0.04 | 0.14 ± 0.13 |
| 2 | 0.13 ± 0.22 | 0.28 ± 0.24 |
| 3 | 0.56 ± 0.60 | 0.93 ± 0.68 |
| 4 | 0.95 ± 0.91 | 1.67 ± 1.14 |
| 5 | 1.68 ± 1.29 | 2.16 ± 1.25 |
| 24 | 6.81 ± 3.30 | 8.11 ± 3.42 |

The results showed that both compositions provided some time dependent penetration of the cromoglicate from the compositions, with up to 6% achieved after 24 hours for the comparative composition and up to 8% achieved after 24 hours for the composition of Example 1.

Conclusions

The tests clearly demonstrate that the composition of Example 1 (a composition of the invention), provides good penetration/absorption of sodium cromoglicate on multiple different membranes achieving levels that were typically better than the comparative composition.

The high level of absorption shown by the compositions of the invention would be expected to be further enhanced when used to treat conditions such as atopic dermatitis because the in vitro tests do not take account of the effect that rubbing the product into the skin, which is known to aid splitting of the composition into water and oil phases, occluding the cromoglicate in the aqueous phase and therefore aiding absorption. Also, in atopic dermatitis the skin barrier is compromised hence further aiding penetration.

EXAMPLE 5

Long Term Stability of a Composition of the Invention

An example of the composition of the invention was prepared as described in Example 1.

The composition of the invention comprises an amphoteric surfactant an alkoxylated cetyl alcohol and a polar drug, wherein the total amount of preservative present in the composition is about 0.2% w/w or less of the composition and is prepared as detailed in Example 1. The condition that the compositions were tested under are summarised in Table 9.

Batches subjected to long term stability testing were as follows.

TABLE 9

| Batch Number | Orientation | Conditions | |
|---|---|---|---|
| | Test condition details of a composition of the invention comprising about 0.2% w/w or less of at least one preservative. | | |
| 1 | Upright | 25° C./60% RH | 5 |
| | | 30° C./65% RH | |
| | | 40° C./75% RH | |
| 2 | Upright | 25° C./60% RH | |
| | | 30° C./65% RH | 10 |
| | | 40° C./75% RH | |

The stability specification that the compositions were assessed under is presented in Table 10.

TABLE 10

Stability specification (House refers to the in-house standard and Ph. Eur refers to the standard set out in the European Pharmacopoeia).

| Attribute | | Specification | Monograph | Method/Comment |
|---|---|---|---|---|
| Appearance | | A smooth, white lotion free from particulate contamination. Product is uniform and has not separated | House | Visual |
| Identification: Sodium Cromoglicate | UV/ Visible | The ratio of absorbance at 239 nm and 327 nm is between 0.25-0.30 | House | UV/VIS Not routinely tested |
| | Chemical/ colourmetric | A yellow/green colour is produced | House | Chemical/ colourmetric. Not routinely tested |
| | HPLC | The peak in the sample chromatogram has the same retention time as the peak in the standard chromatogram | House | HPLC Not routinely tested |
| Assay of Sodium Cromoglicate (% w/w) | | 3.8-4.2 | House | HPLC |
| Chlorocresol (% w/w) | | 0.10-0.12 (release) 0.08-0.12 (shelf life) | House | HPLC |
| pH at 20° C. | | 3.8-5.8 | House | pH meter |
| Penetration at 25° C. (tenths mm) | | 100-300 | House | Penetrometer |
| *Kromo I (% w/w relative to Sodium Cromoglicate) | | Not greater than 0.20 | House | HPLC |
| *Kromo II (% w/w relative to Sodium Cromoglicate) | | Not greater than 0.20 | House | HPLC |
| *Oxalate (% w/w relative to Sodium Cromoglicate) | | Not more than 0.10 | House | Ion Chromatography |
| Any individual unknown degradant (% w/w relative to sodium Cromoglicate) | | Not more than 0.10 | House | HPLC |
| *Total specified degradants (% w/w relative to Sodium Cromoglicate) | | Not more than 0.50 | House | HPLC/Ion Chromatography |
| Total degradation products (% w/w relative to Sodium Cromoglicate) | | Not more than 1.0 | House | HPLC/Ion Chromatography |
| Total Aerobic Microbial Cotint | | Not more than $10^2$ aerobic organisms/gram (colony forming units per gram) | Ph. Eur. | Ph. Eur. |
| Total Yeasts & Mould Count | | Not more than $10^3$ yeasts & mould/gram (colony forming units per gram) | Ph. Eur. | Ph. Eur. |
| Absence of Enterobacteriaceae | | Absent in 1 gm | Ph. Eur. | Ph. Eur. |
| Absence of *Pseudomonas aeruginosa* | | Absent in 1 gm | Ph. Eur. | Ph. Eur. |
| Absence of *Staphylococcus aureus* | | Absent in 1 gm | Ph. Eur. | Ph. Eur. |
| Preservative Efficacy Ph. Eur. Topical preparations- Criteria A | | Complies | Ph. Eur. | Ph. Eur. Performed only on batch 2359 |

*no longer tested

Summary of Stability Data on the Composition of the Invention

A summary of stability data on the composition of the invention as prepared in Example 1. The results are shown in Table 11.

Appearance

Remains in specification throughout 36 months testing.

Assay of Sodium Cromoglicate (% w/w)

Remains in specification throughout 36 months testing. No trend apparent at any storage condition.

Chlorocresol (% w/w)

This attribute trends downwards significantly at accelerated conditions. The initial shelf life specification of 0.10-0.12% w/w was reset to 0.08-0.12% w/w on the basis of stability test results (preservative efficacy testing having established that this level provided adequate preservation). All batches remained in specification to 36 months at this condition.

pH at 20° C.

Remains in specification throughout 36 months testing. No trend apparent at any storage condition.

Penetration at 25° C.

Remains in specification throughout 36 months testing.

Kromo I (% w/w Relative to Sodium Cromoglicate)

Remains in specification throughout 36 months testing. No trend apparent at any storage condition.

Kromo II (% w/w Relative to Sodium Cromoglicate)

Remains in specification throughout 36 months testing. No trend apparent at any storage condition.

Oxalate (% w/w Relative to Sodium Cromoglicate)

Remains in specification throughout 36 months testing. No trend apparent at any storage condition.

TABLE 11

| | | Results of Stability Tests | | |
| | | | Long term stability testing - upright storage Batches DEV2359, DEV2360 | |
| Attribute | Specification | 25° C./60% RH to 36 months | 30° C./65% RH to 36 months | 40° C./75% RH to 36 months |
| --- | --- | --- | --- | --- |
| Appearance | Smooth, white lotion free from particulate contamination | Complies | Complies | Complies |
| Assay of Sodium Cromoglicate (% w/w) | 3.8-4.2 | 3.8-4.1 | 3.8-4.1 | 3.9-4.2 |
| Chlorocresol (% w/w) | 0.08-0.12 | 0.10-0.11 | 0.10-0.11 | 0.06-0.11 |
| pH at 20° C. | 3.8-5.8 | 4.7-5.0 | 4.1-4.9 | 4.7-5.0 |
| Penetration at 25° C. (tenths min) | 100-300 | 105-215 | 121-227 | 115-234 |
| Kromo I (% w/w relative to Sodium Cromoglicate) | Not greater than 0.20 | None detected | None detected | None detected |
| Kromo II (% w/w relative to Sodium Cromoglicate) | Not greater than 0.20 | None detected | None detected | None detected |
| Oxalate relative to Sodium Cromoglicate) | Not more than 0.10 | 0.035-0.046 | 0.035-0.047 | 0.036-0.049 |
| Any individual unknown degradant (% w/w relative to Sodium Cromoglicate) | Not more than 0.10 | None detected | None detected | None detected |
| Total specified degradants (% w/w relative to Sodium Cromoglicate) | Not more than 0.50 | 0.033-0.045 | 0.035-0.047 | 0.036-0.049 |
| Total degradation products (% w/w relative to Sodium Cromoglicate) | Not more than 1.0 | 0.033-0.045 | 0.035-0.047 | 0.036-0.049 |
| Total Viable Count | Not more than $10^2$ aerobic microorganisms per gram (colony forming units per gram) | Complies | Complies | — |
| Absence of Enterobacteriaceae | Absent in 1 gm | Complies | Complies | — |
| Absence of *Pseudomonas aeruginosa* | Absent in 1 gm | Complies | Complies | — |
| Absence of *Staphylococcus aureus* | Absent in 1 gm | Complies | Complies | — |
| Preservative Efficacy Ph. Ear. Topical preparations- Criteria A | Complies | Pass | Pass | — |

Any Individual Unknown Degradant (% w/w Relative to Sodium Cromoglicate)

Remains in specification throughout 36 months testing. No trend apparent at any storage condition.

Total Specified Degradants (% w/w Relative to Sodium Cromoglicate)

Remains in specification throughout 36 months testing. No trend apparent at any storage condition.

Total Degradation Products (% w/w Relative to Sodium Cromoglicate)

Remains in specification throughout 36 months testing. No trend apparent at any storage condition, Total Viable Count Remains in specification throughout 36 months (testing at 25° C./60% RH and 30° C./65% RH only).

Absence of *Enterobacteriaceae, Pseudomonas aeruginosa* and *Staphylococcus aureus*

Remains in specification throughout 36 months (testing at 25° C./60% RH and 30° C./65% R only).

Preservative Efficacy pH. Eur. Topical Preparations—Criteria A

Performed only on batch 2359. Remains in specification throughout 36 months (testing at 25° C./60% RH and 30° C./65% RH only).

Freeze-Thaw Cycling

Freeze-Thaw cycling has not been performed on this product. It is not considered necessary—it is well established that emulsions of this type are not physically stable and will crack when frozen.

In Use Stability Tests

In-use stability testing was performed to replicate use over 56 days at 25° C./60% RH. The testing included two aged batches (24 and 36 months) of the composition of the invention prepared as defined in Example 1. All parameters tested remained in specification at 56 days all both batches tested. The results are presented in Tables 12, 13 and 14 below.

TABLE 12

Stability of a composition of the invention in use over 56 at 25° C./60% RH in a 150 ml plinth HDPE white round bottle with Model 7 pump dispenser.

| Attribute | Specification | Initial | 56 Days |
|---|---|---|---|
| Appearance | Smooth, white lotion free from particulate | Complies | Complies |
| Assay of Sodium Cromoglicate (% w/w) | 3.8-4.2 | 4.0 | 3.9 |
| Chlorocresol (% w/w) | 0.10-0.12 | 0.11 | 0.11 |
| pH at 20° C. | 3.8-5.8 | 4.8 | 4.7 |
| Kromo I (% w/w relative to Sodium Cromoglicate) | Not greater than 0.20 | None detected | None detected |
| Kromo II (% w/w relative to Sodium Cromoglicate) | Not greater than 0.20 | None detected | None detected |
| Oxalate relative to Sodium Cromoglicate | Not more than 0.10 | 0.037 | 0.040 |
| Any individual unknown degradant (% w/w relative to Sodium Cromoglicate) | Not more than 0.10 | None detected | None detected |
| Total specified degradants (% w/w relative to Sodium Cromoglicate) | Not more than 0.50 | 0.037 | 0.040 |
| Total degradation products (% w/w relative to Sodium Cromoglicate) | Not more than 1.0 | 0.037 | 0.040 |
| *Total Viable Count | Not more than $10^2$ aerobic organisms/gram | Complies | Complies |
| Absence of Enterobacteriaceae | Absent in 1 gm | Complies | Complies |
| Absence of *Pseudomonas aeruginosa* | Absent in 1 gm | Complies | Complies |
| Absence of *Staphylococcus aureus* | Absent in 1 gm | Complies | Complies |
| Preservative Efficacy Ph. Eur. Topical preparations- Criteria A | Complies | Complies | Complies |

*Weekly microbiological testing was also passed at each time point

TABLE 13

Stability of a composition of the invention aged for 24 months in use over 56 at 25° C./60% RH in a 150 ml plinth HDPE white round bottle with Model 7 pump dispenser.

| Attribute | Specification | Initial | 56 Days |
|---|---|---|---|
| Appearance | Smooth, white lotion free from particulate | Complies | Complies |
| Assay of Sodium Cromoglicate (% w/w) | 3.8-4.2 | 4.1 | 3.9 |
| Chlorocresol (% w/w) | 0.10-0.12 | 0.10 | 0.10 |
| pH at 20° C. | 3.8-5.8 | 4.8 | 4.9 |
| Penetration at 25° C. (tenths min) | 100-300 | 140 | 157 |
| Kromo I (% w/w relative to Sodium Cromoglicate) | Not greater than 0.20 | None detected | None detected |
| Kromo II (% w/w relative to Sodium Cromoglicate) | Not greater than 0.20 | None detected | None detected |
| Oxalate relative to Sodium Cromoglicate | Not more than 0.10 | 0.042 | 0.043 |

TABLE 13-continued

Stability of a composition of the invention aged for 24 months in use over 56 at 25°
C./60% RH in a 150 ml plinth HDPE white round bottle with Model 7 pump dispenser.

| Attribute | Specification | Initial | 56 Days |
|---|---|---|---|
| Any individual unknown degradant (% w/w relative to Sodium Cromoglicate) | Not more than 0.10 | None detected | None detected |
| Total specified degradants (% w/w relative to Sodium Cromoglicate) | Not more than 0.50 | 0.042 | 0043 |
| Total degradation products (% w/w relative to Sodium Cromoglicate) | Not more than 1.0 | 0.042 | 0.043 |
| Total Viable Count | Not more than $10^2$ aerobic organisms/gram | Complies | Complies |
| Absence of Enterobacteriaceae | Absent is 1 gm | Complies | Complies |
| Absence of *Pseudomonas aeruginosa* | Absent is 1 gm | Complies | Complies |
| Absence of *Staphylococcus aureus* | Absent is 1 gm | Complies | Complies |
| Preservative Efficacy Ph. Eur. Topical preparations- Criteria A | Complies | — | Complies |

TABLE 14

Stability of a composition of the invention aged for 36 months in use over 56 at 25°
C./60% RH in a 150 ml plinth HDPE white round bottle with Model 7 pump dispenser.

| Attribute | Specification | Initial | 56 Days |
|---|---|---|---|
| Appearance | Smooth, white lotion free from particulate | Complies | Complies |
| Assay of Sodium Cromoglicate (% w/w) | 3.8-4.2 | 3.9 | 4.0 |
| Chlorocresol (% w/w) | 0.10-0.12 | 0.11 | 0.11 |
| pH at 20° C. | 3.8-5.8 | 5.0 | 4.8 |
| Penetration at 25° C. (tenths min) | 100-300 | 148 | 193 |
| Kromo I (% w/w relative to Sodium Cromoglicate) | Not greater than 0.20 | None detected | None detected |
| Kromo II (% w/w relative to Sodium Cromoglicate) | Not greater than 0.20 | None detected | None detected |
| Oxalate relative to Sodium Cromoglicate) | Not more than 0.10 | 0.042 | 0.039 |
| Any individual unknown degradant (% w/w relative to Sodium Cromoglicate) | Not more than 0.10 | None detected | None detected |
| Total specified degradants (% w/w relative to Sodium Cromoglicate) | Not more than 0.50 | 0.042 | 0.039 |
| Total degradation products (% w/w relative to Sodium Cromoglicate) | Not more than 1.0 | 0.042 | 0.039 |
| Total Viable Count | Not more than $10^2$ aerobic organisms/gram | Complies | Complies |
| Absence of Enterobacteriaceae | Absent to 1 gm | Complies | Complies |
| Absence of *Pseudomonas aeruginosa* | Absent to 1 gm | Complies | Complies |
| Absence of *Staphylococcus aureus* | Absent to 1 gm | Complies | Complies |
| Preservative Efficacy Ph. Ear. Topical preparations- Criteria A | Complies | Pass | Pass |

*Weekly microbiological testing was also passed at each time point

Forced Degradation

Forced degradation studies of the product with add, base and peroxide were performed as a screen for potential degradation products. The samples were evaluated by LCMSMS.

The samples were mixed with acid, base or peroxide and left overnight. The samples were then diluted with water and filtered.

The samples were then analysed using LCMSMS. The samples were run on an Agilent 1290 with Agilent 6530 qTOF mass spectrometry.

The chromatograms were compared and any evidence of new peaks when compared to the relevant controls were recorded and their mass determined.

Significant degradation was seen only in alkaline solution. The structure of cromoglicate is such assignment of struc-tures is difficult. The molecular formulas of theses degra-dation peaks have been calculated but they cannot be assigned to an individual structure. As sodium cromoglicate is well known, and as Altocrom in use will not be exposed to strongly alkaline conditions, the inability to assign struc-tures is not considered important.

Proposed Shelf Life

The proposed shelf life is 36 months when the product is stored at a temperature not exceeding 25° C.

The invention claimed is:

1. A composition for topical administration for use in treating a skin disease or condition, wherein the skin disease or condition involves skin mast cells, delayed hypersensi-tivity reactions, or inflammation, or is selected from atopic dermatitis, eczema, contact sensitivity, psoriasis, drug sen-sitivity reactions, aphthous ulcers, pemphigus, urticaria, urticaria pigmentosa, pyoderma gangrenosum, skin ulcers associated with Crohn's disease, burns, insect stings/bites, morphoea, and sunburn, or a combination thereof, and wherein the composition comprises sodium cromoglicate, an amphoteric surfactant, and an alkoxylated cetyl alcohol, wherein the total amount of a preservative present in the composition is about 0.2% w/w or less wherein the preservative is chlorocresol and is not one or more of benzyl alcohol and triclosan.

2. The composition according to claim 1, wherein the total amount of preservative is selected from
    a) about 0.001% to about 0.2% w/w of the composition,
    b) about 0.01% to about 0.15% w/w of the composition, or
    c) about 0.1% w/w of the composition.

3. The composition according to claim 1, wherein the amphoteric surfactant is a balanced amphoteric surfactant.

4. The composition according to claim 1, wherein the alkoxylated cetyl alcohol is polypropoxylated cetyl alcohol.

5. The composition according to claim 1, wherein the amphoteric surfactant comprises disodium cocoamphodiacetate.

6. The composition according to claim 1, further comprising a corticosteroid.

7. The composition according to claim 1, wherein the composition comprises an aqueous phase and an oil phase.

8. The composition according to claim 7, wherein the composition is an oil-in-water emulsion.

9. The composition according to claim 1, wherein the composition is a foam, a cream, an ointment, or a lotion.

10. The composition according to claim 1, packaged in a tube, tub, bottle, or pressurized aerosol container.

11. A method for treating a skin disease or condition selected from one or more of atopic dermatitis, eczema, contact sensitivity, psoriasis, drug sensitivity reactions, aphthous ulcers, pemphigus, urticaria, urticaria pigmentosa, pyoderma gangrenosum, skin ulcers associated with Crohn's disease, burns, insect stings/bites, morphoea, and sunburn comprising administering the composition according to claim 1.

12. The method according to claim 11, further comprising administering a corticosteroid.

13. The method according to claim 12, wherein the corticosteroid is incorporated into the composition or administered as a separate composition.

14. A composition for topical administration comprising:
    a) sodium cromoglicate;
    b) an amphoteric surfactant;
    c) an alkoxylated cetyl alcohol, and
    d) a preservative in an amount selected from
        i) about 0.001% to about 0.2% w/w of the composition,
        ii) about 0.01% to about 0.15% w/w of the composition, or
        iii) about 0.1% w/w of the composition;
wherein the preservative is chlorocresol and is not one or more of benzyl alcohol and triclosan.

15. The composition of claim 14, wherein the amphoteric surfactant comprises disodium cocoamphodiacetate; the alkoxylated cetyl alcohol is polypropoxylated cetyl alcohol.

16. The composition of claim 14, further comprising a corticosteroid.

17. A composition for treating a skin disease or condition selected from the group consisting of one or more of atopic dermatitis, eczema, contact sensitivity, psoriasis, urticaria, urticaria pigmentosa, burns, and sunburn, comprising administering a composition comprising: sodium cromoglicate, an amphoteric surfactant, and an alkoxylated cetyl alcohol, wherein the total amount of a preservative present in the composition is about 0.2% w/w or less, wherein the preservative is chlorocresol and is not one or more of benzyl alcohol and triclosan.

18. A method of treating a skin disease or condition selected from the group consisting of one or more of atopic dermatitis, eczema, contact sensitivity, psoriasis, urticaria, urticaria pigmentosa, burns, and sunburn, comprising administering a composition comprising: sodium cromoglicate, an amphoteric surfactant, and an alkoxylated cetyl alcohol, wherein the total amount of a preservative present in the composition is about 0.2% w/w or less, wherein the preservative is chlorocresol and is not one or more of benzyl alcohol and triclosan.

* * * * *